Aug. 20, 1935. T. J. WOLFE Plant Pat. 134
ROSE
Filed March 22, 1935
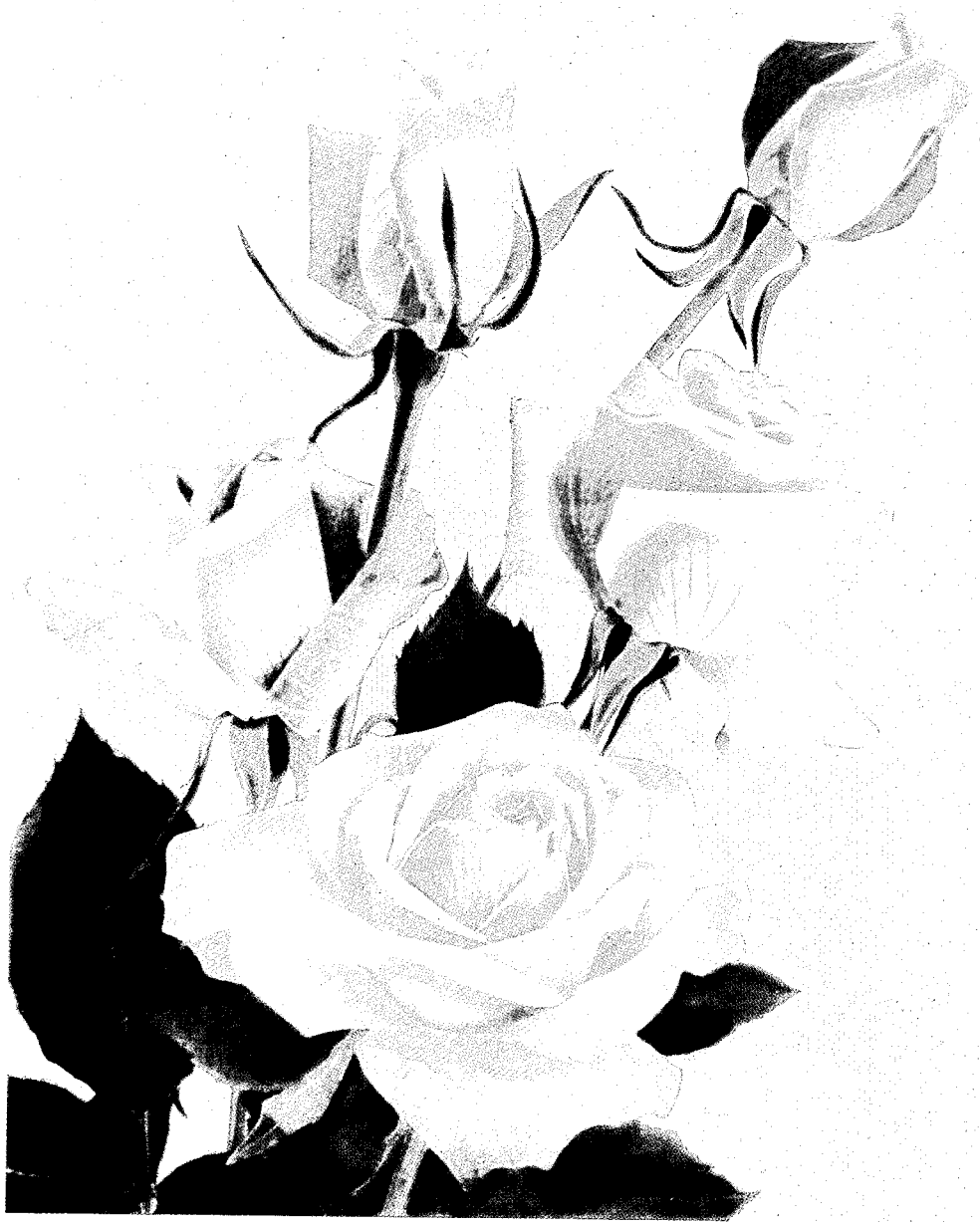
Inventor
Thomas James Wolfe
By Robert Tobey
attorney Patented Aug. 20, 1935

UNITED STATES PATENT OFFICE

134

ROSE

Thomas James Wolfe, Waco, Tex.

Application March 22, 1935, Serial No. 12,512

1 Claim. (Cl. 47—61)

The present discovery relates to a new and distinct variety of hybrid Tea rose originating as a sport from the rose known as "Better Times", disclosed in Plant Patent No. 23.

This new variety of rose possesses many of the characteristics of such other sport roses as "Columbia", "Rose Hill" and "Briarcliff", speaking with reference to their very heavy and prolific habits of growth, but it possesses several individual distinctions which mark it as an improvement in the class of plants useful as cut flowers.

In addition to the above general characteristics, I desire it to be noted that the present invention has many fine qualities distinguishing it from its parent "Better Times." In the first place, in color, it belongs in the range of a lighter pink, "Better Times" being a cerise or a watermelon red, and it is the particularly pleasing shade of pink color which is the most desirable and most popular in flowers now well known in commerce. This is important when considered from the standpoint of its adaptability as a forcing rose, the color being brighter and different by several shades than the known popular roses of this same class. Furthermore it is stressed that this color of the rose above mentioned in the new variety does not turn purple-blue when very old as most flowers of this color range do, so that from the standpoint of a cut flower it is clearly distinguished from its predecessors.

The new variety possesses unusual qualities as a shipper because of its greater endurance and ability to stand abuse. Shipments of the rose have been made by mail in ordinary wrappings, not particularly designed to shield the roses from changes in temperature to long distances, arriving at destination in temperatures much below zero, yet its appearance has been in no wise injured, as exemplified by the reproduction of the drawing herewith, made after one of such shipments.

Taking into consideration the before mentioned characteristics, of color, of foliage and its thornlessness, together with its keeping qualities, the present rose becomes an important addition to the rose family.

The characteristics herein described appear to be permanently fixed, as determined by asexual reproduction.

The following is a detail description of this new variety of rose plant:

Parentage:

Sport of variety "Better Times".

Classification:

Botanic and commercial—Hybrid tea.

*Flower*

Blooming habit:

Blooms profusely.

Recurrent—Continuous. Other habit, large flower. Will not blue when old; keeping quality very, very fine; prolific grower and bloomer; disease resistant; flowers are very double on long stems from natural cut.

Bud:

*Size.*—Very large.

*Form.*—Ovoid. Unaffected by wet or hot weather.

*Color.*—When sepals first divide dark purpled pink to china pink. When petals begin to unfurl purpled pink to china pink. When half blown inside of petals china pink to violet pink to vinous pink; reverse side of petals dark china to dark violet pink to vinous pink. (Name of color standard used Gravereaux system.)

*Sepals.*—Smooth edge, hood above bud; curl back when half open.

*Calyx.*—Shape funnel to pear. Size large. Aspect—Outer smooth and inner hairy. Odor when rubbed faint suggestion tea leaves.

*Peduncle.*—Medium length. Aspect smooth. Color medium green. Strength stiff to erect. Opening bud opens perfect. Unaffected by adverse conditions.

Bloom:

*Size.*—Very large; average size when fully opened about five inches or larger.

*Borne.*—Singly.

*Stems.*—Long, strong.

*Form.*—When first open flat to high center. Permanence—retains its form to the end; flattens and cups slightly.

*Petalage.*—Very double (many petals and stamens hidden). Number of petals under normal conditions 50 or more including petaloids.

*Color.*—Center of flower china pink to violet pink. Outer petals purpled pink to violet pink. Base of petals (aiglet) light nasturtium. Inside of petals purpled pink to violet pink. Reverse of petals silvery—combination purpled pink and violet pink with silvery tone. General tonality from a distance china to purpled pink.

*Variegations.*—Veined.

*Discoloration.*—General tonality at end:—Second day same as first day. Third day lightens slightly.

Petals:

*Texture.*—Thick; unaffected by wet or hot weather.

*Appearance.*—Inside shiny to satiny; outside shiny to satiny.

*Form.*—Round.

*Arrangement.*—Imbricated (regularly arranged shingle like). Petaloids in center many, large.

*Persistence.*—Hang on and dry.

*Fragrance.*—Moderate tea.

*Lasting quality.*—On the plant very long and as a cut flower very long.

Genital organs:

*Stamens, anthers.*—Medium, many. Color—white to light yellow. Arrangement—mixed with petaloids.

*Stamens, filaments (threads) medium.*—Color—reddish.

*Pollen.*—Lemon yellow.

*Styles.*—Bunched, medium length.

*Stigmas.*—Color, light yellow tinged red.

*Ovaries.*—Some protruding from calyx.

*Plant*

Form:

Bush.

Growth:

Very vigorous.

Foliage:

Leaflets mostly five—few seven.

*Size.*—Very large.

*Quantity.*—Abundant.

*Color.*—New foliage—upper side bronzy; under side purple bronzy. Old foliage—upper side normal green; under side light green.

*Shape.*—Round to oval.

*Texture.*—Upper side leathery, glossy, smooth; under side slightly velvety; ribs and veins ordinary.

*Edge.*—Serrated to saw toothed. Mature foliage is fringed or scalloped and because of slight undulations in the surface it suggests holly leaf type.

*Serration.*—Single, small, sharp.

*Leaf stem.*—Reddish color; under side smooth.

*Stipules.*—Long to medium, smooth.

*Disease resistance.*—Resistant.

Wood:

*New wood.*—Color bronzy; bark smooth.

*Old wood.*—Color green to brown; bark smooth.

Thorns:

*Thorns.*—Quantity—on main stalks from base few to none; on laterals from stalk none. Form—flat base; short; hooked downward. Color when young—green and red. Position—irregular.

*Prickles.*—Quantity—on main stalks none.

*Short needles.*—Quantity—on main stalks few to none. On laterals none.

I claim:

A new and distinct variety of hybrid tea rose plant, characterized by the shape and fringed character of its foliage, its lack of thorns, and the very large, double, unfading and novel color flowering habit on long strong stems, substantially as shown and described.

THOMAS JAMES WOLFE,